United States Patent
Kamalakaran et al.

(10) Patent No.: US 11,264,118 B2
(45) Date of Patent: Mar. 1, 2022

(54) METHODS OF DISPLAYING THE ANTIMICROBIAL SENSITIVITY OF BIOLOGICAL ISOLATES

(71) Applicant: KONINKLIJKE PHILIPS N.V., Eindhoven (NL)

(72) Inventors: Sitharthan Kamalakaran, Pelham, NY (US); Pramod Mayigowda, White Plains, NY (US); Henry Lin, Quincy, MA (US); Sonia Chothani, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 302 days.

(21) Appl. No.: 15/557,628

(22) PCT Filed: Mar. 10, 2016

(86) PCT No.: PCT/IB2016/051352
§ 371 (c)(1),
(2) Date: Sep. 12, 2017

(87) PCT Pub. No.: WO2016/142890
PCT Pub. Date: Sep. 15, 2016

(65) Prior Publication Data
US 2018/0293349 A1    Oct. 11, 2018

Related U.S. Application Data

(60) Provisional application No. 62/132,199, filed on Mar. 12, 2015.

(51) Int. Cl.
*G16B 45/00* (2019.01)
*B61L 5/10* (2006.01)
*C12Q 1/18* (2006.01)

(52) U.S. Cl.
CPC ............ *G16B 45/00* (2019.02); *B61L 5/10* (2013.01); *C12Q 1/18* (2013.01)

(58) Field of Classification Search
CPC ............ G16B 45/00; B61L 5/10; C12Q 1/18
USPC .......................................................... 702/19
See application file for complete search history.

(56) References Cited

U.S. PATENT DOCUMENTS

2015/0344973 A1   12/2015   Clarke et al.

FOREIGN PATENT DOCUMENTS

| JP | 2005228171 A | 8/2005 |
|---|---|---|
| WO | 2005024550 A2 | 3/2005 |

OTHER PUBLICATIONS

Krucso, et al., "Molecular characterisation of invasive *Streptococcus pyogenes* isolates from Hungary obtained in 2004 and 2005", European Journal of Clinical Microbiology & Infectious Diseases, vol. 26, No. 11, Jul. 31, 2007, pp. 807-811.

*Primary Examiner* — Jerry Lin

(57) ABSTRACT

Methods and systems for monitoring and determining antimicrobial resistance and antimicrobial treatment using genomic subtype information. Various embodiments utilize molecular epidemiology and next-generation sequencing technologies (NGS) to monitor multi-drug resistant pathogens and provide early insight into emergent microbial threats.

15 Claims, 2 Drawing Sheets

METHODS OF DISPLAYING THE ANTIMICROBIAL SENSITIVITY OF BIOLOGICAL ISOLATES

CROSS-REFERENCE TO PRIOR APPLICATIONS

This application is the U.S. National Phase application under 35 U.S.C. § 371 of International Application No. PCT/IB2016/051352 filed on Mar. 10, 2016, which claims the benefit of U.S. Provisional Application Ser. No. 62/132,199, filed Mar. 12, 2015. These applications are hereby incorporated by reference, for all purposes.

FIELD

Various embodiments described herein generally relate to the creation and display of antibiograms, and more specifically to the creation and display of antibiograms with subtyped organisms.

BACKGROUND

Infectious diseases (IDs) cause widespread morbidity and mortality. A review of the Nationwide Inpatient Sample for 1998-2006 estimated 40 million hospitalizations with ID as the primary condition. Recent studies estimate that up to 51% of ICU patients are suffering from an infectious disease with 71% of intensive care unit (ICU) patients receiving antimicrobials. The mortality of patients with infections is twice that of those who are infection-free.

Moreover, nosocomial infections (i.e., infections acquired by a patient in the hospital) are estimated to occur in 5% of all acute care hospitalizations. This equates to more than 2 million cases per year, associated with added expenditures in excess of $4.5 billion. Nosocomial infections can cause severe pneumonia and infections of the urinary tract, bloodstream and other parts of the body.

Many types of nosocomial infections are difficult to attack with antimicrobials. Antimicrobials have been used extensively over the last 70 years to reduce the number of deaths due to infectious diseases. However, the drugs have been used so widely and for so long that the infectious organisms the antimicrobials are designed to kill have instead adapted to the antimicrobials, making the drugs less effective.

The American Centers for Disease Control (CDC) reports that 30-50% of the antimicrobials prescribed in hospitals are unnecessary or inappropriate. Overprescribing and misprescribing antimicrobials is contributing to the growing challenges posed by the antimicrobial resistant bacteria. The CDC also reports that improving prescription practices in hospitals can not only help reduce rates of hospital acquired infection and antimicrobial resistance, but can also improve individual patient outcomes, all while reducing healthcare costs.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

Given the rise of antimicrobial resistant bacteria, there is a need for methods and systems that allow for the improved management of antimicrobials and antimicrobial-resistant infections, especially in a clinical environment.

A hospital antibiogram is, generally, a periodic summary of antimicrobial susceptibilities of local bacterial isolates submitted to a hospital's clinical microbiology laboratory. Antibiograms are often used by clinicians to assess local susceptibility rates, as an aid in selecting empiric antimicrobial therapy, and in monitoring resistance trends over time within an institution. Antibiograms can also be used to compare susceptibility rates across institutions and track resistance trends. Keeping track of this information is important to monitor emerging trends in antimicrobial resistance and support clinical decision making, infection-control strategies, and resistance containment strategies.

Various embodiments generally relate to the creation of antibiograms using genomic subtype information. More specifically, some embodiments utilize molecular epidemiology and next-generation sequencing technologies (NGS) to monitor multi-drug resistant pathogens, determine their antimicrobial resistance, provide early insight into emergent microbial threats, and recommend antimicrobial treatments.

Generally speaking, pathogens and other microbes of interest are cultured and tested for sensitivity (or conversely, resistance) to various antimicrobials. The cultured pathogens are sequenced (e.g., by whole genome sequencing, targeted sequencing, etc.) and their genomic data (e.g., a Fasta sequence file) is compared against a publicly-accessible or private database of genomic data to identify the particular subtype of the tested pathogens. The sensitivity/resistance data according to subtype is then presented to the user using a novel user interface.

Some embodiments relate to a computer-implemented method for generating a subtype-specific display. The method includes providing a computer processor configured to receive information concerning the sensitivity of at least one isolate to at least one antimicrobial; to receive information concerning the subtype of the at least one isolate; and provide a graphical display of the sensitivity of the at least one isolate to the at least one antimicrobial organized by subtype.

In one embodiment, receiving information concerning the subtype of the at least one isolate comprises receiving data describing at least part of the genome of the at least one isolate; comparing the received genomic data from the sequencing operation against a reference database; and identifying a matching subtype for the at least one isolate from the results of the comparison.

In one embodiment, receiving information concerning the sensitivity of the at least one isolate to the at least one antimicrobial comprises receiving the results of an antimicrobial sensitivity test for the at least one isolate utilizing the at least one antimicrobial. In one embodiment, providing a graphical display of the sensitivity of the at least one isolate to the at least one antimicrobial organized by subtype comprises providing a graphical display in a matrix configuration with each row associated with one subtype and each column associated with one antimicrobial. In another embodiment, providing a graphical display of the sensitivity of the at least one isolate to the at least one antimicrobial organized by subtype comprises providing a graphical display in a matrix configuration with each column associated with one subtype and each row associated with one antimicrobial.

In one embodiment, providing a graphical display of the sensitivity of the at least one isolate to the at least one antimicrobial organized by subtype comprises providing a graphical display of colored items in a matrix configuration.

In one embodiment, providing a graphical display of the sensitivity of the at least one isolate to the at least one antimicrobial organized by subtype comprises providing a graphical display of numbers in a matrix configuration. In one embodiment, each number is the prevalence of that isolate in a population in a particular timeframe and the sensitivity ratio for that isolate is displayed as a color or a shaded circle. In one embodiment, each number is the number of isolates from which the sensitivity-to-resistance ratio for a particular subtype against a particular antimicrobial was drawn. In one embodiment, each number is the sensitivity-to-resistance ratio for a subtype against an antimicrobial. In one embodiment, each number is an average sensitivity for a plurality of isolates of a particular subtype against a particular antimicrobial. In one embodiment, each number is the incidence or prevalence of that subtype in the time period under review.

In another aspect, various embodiments relate to a computer readable medium containing computer-executable instructions for performing a method for generating a subtype-specific display. The medium comprises computer-executable instructions for receiving information concerning the sensitivity of at least one isolate to at least one antimicrobial; computer-executable instructions for receiving information concerning the subtype of the at least one isolate; and computer-executable instructions for providing a graphical display of the sensitivity of the at least one isolate to the at least one antimicrobial organized by subtype.

In one embodiment, the computer-executable instructions for receiving information concerning the subtype of the at least one isolate comprise computer-executable instructions for receiving data describing at least part of the genome of the at least one isolate; computer-executable instructions for comparing the received genomic data from the sequencing operation against a reference database; and computer-executable instructions for identifying a matching subtype for the at least one isolate from the results of the comparison.

In one embodiment, the computer-executable instructions for receiving information concerning the sensitivity of the at least one isolate to the at least one antimicrobial comprise computer-executable instructions for receiving the results of an antimicrobial sensitivity test for the at least one isolate utilizing the at least one antimicrobial. In one embodiment, the computer-executable instructions for providing a graphical display of the sensitivity of the at least one isolate to the at least one antimicrobial organized by subtype comprise computer-executable instructions for providing a graphical display in a matrix configuration with each row associated with one subtype and each column associated with one antimicrobial. In another embodiment, the computer-executable instructions for providing a graphical display of the sensitivity of the at least one isolate to the at least one antimicrobial organized by subtype comprise computer-executable instructions for providing a graphical display in a matrix configuration with each column associated with one subtype and each row associated with one antimicrobial.

In one embodiment, the computer-executable instructions for providing a graphical display of the sensitivity of the at least one isolate to the at least one antimicrobial organized by subtype comprises computer-executable instructions for providing a graphical display of colored items in a matrix configuration. In one embodiment, the computer-executable instructions for providing a graphical display of the sensitivity of the at least one isolate to the at least one antimicrobial organized by subtype comprises computer-executable instructions for providing a graphical display of numbers in a matrix configuration. In one embodiment, each number is the prevalence of that isolate in a population in a particular timeframe and the sensitivity ratio for that isolate is displayed as a color or a shaded circle. In one embodiment, each number is the number of isolates from which the sensitivity-to-resistance ratio for a particular subtype against a particular antimicrobial was drawn. In one embodiment, each number is the sensitivity-to-resistance ratio for a subtype against an antimicrobial. In one embodiment, each number is an average sensitivity for a plurality of isolates of a particular subtype against a particular antimicrobial. In one embodiment, each number is the incidence or prevalence of that subtype in the time period under review.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

Non-limiting and non-exhaustive embodiments are described with reference to the following figures in which.

In the drawings, like reference characters generally refer to corresponding parts throughout the different views. The drawings are not necessarily to scale, emphasis instead being placed on the principles and concepts of operation.

DETAILED DESCRIPTION

Figure 1:
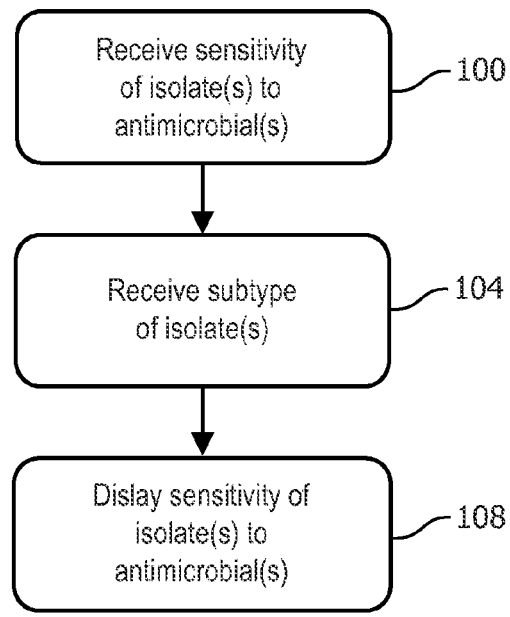
FIG. 1 depicts an example of one embodiment of a method for antibiogram generation.

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems or devices. Accordingly, embodiments may take the form of a hardware implementation, an entirely software implementation (which will nonetheless be understood to operate on supporting hardware such as a processor) or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one embodiment. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are the means used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Various embodiments include process steps and instructions that could be embodied in software, firmware or hardware, and when embodied in software, could be downloaded to reside on and be operated from different platforms used by a variety of operating systems.

The present disclosure also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. As used herein, the term 'processor' will be understood to encompass microprocessors, field-programmable gate arrays (FPGAs), ASICs, and any other similar devices capable or performing the processing functions described herein. Further, as used herein, the term non-transitory machine-readable medium will be understood to encompass both volatile memory devices (e.g., SRAM and DRAM) and non-volatile memory devices (e.g., flash, magnetic, optical memories), but will exclude transitory signals.

The processes and displays presented herein are not inherently related to any particular computer or other apparatus. Various general purpose systems may also be used with programs in accordance with the teachings herein, or it may prove convenient to construct more specialized apparatus to perform the required method steps. The required structure for a variety of these systems will appear from the description below. In addition, the embodiments disclosed herein are not described with reference to any particular programming language. It will be appreciated that a variety of programming languages may be used to implement the teachings described herein, and any references below to specific languages are provided for disclosure of enablement and best mode.

In addition, the language used in the specification has been principally selected for readability and instructional purposes, and may not have been selected to delineate or circumscribe the inventive subject matter. Accordingly, this disclosure is intended to be illustrative, but not limiting, of the scope of the invention, which is set forth in the claims.

Conventionally, antimicrobials are administered to patients based on a doctor's knowledge and previous experience. In contrast, some embodiments identify an appropriate antimicrobial for the particular subtype of the organism at issue through a combination of NGS technologies and tests for antimicrobial sensitivity. Antimicrobial profiles generated based on organism subtypes not only help the doctor to administer the most appropriate antimicrobial according to patient profiles, but also reduces the cost of antimicrobials and improves patient care.

FIG. 1 is a flowchart of an exemplary method for antibiogram generation. In this example, the process begins when a computing device receives information concerning the sensitivity of at least one isolate to at least one antimicrobial (Step 100). The computing device also receives information concerning the subtype of the at least one isolate (Step 104) although, as discussed below, this information may be received prior to, contemporaneously with, etc., the receipt of the aforementioned sensitivity information. With this information, the computing device provides a display of the sensitivity of the at least one isolate to the at least one antimicrobial organized by subtype (Step 108). In one embodiment, discussed in greater detail below, the display includes the sensitivity of a plurality of isolates to a plurality of antimicrobials, with the isolates organized by subtype.

The sensitivity of the at least one isolate to the at least one antimicrobial (Step 100) can be obtained in a variety of ways. In some embodiments, the information is received via a network connection from a source for such information. In other embodiments, the information is determined by performing one or more microscan antibiotic sensitivity tests (or E-tests based on antimicrobial diffusion, or minimum inhibitory concentration determinations based on agar and broth dilution methods, etc.) on the isolate, or by retrieving the data from such tests from a laboratory information management system (LIMS). In some embodiments, the lowest concentration of antibiotic that prevented growth represents a minimal inhibitory concentration (MIC), and the sensitivity of the at least one isolate can be determine by quantitative or qualitative tests that correlate with a predetermined MIC. In some embodiments, the test results are post-processed to determine, e.g., an average sensitivity level for the isolate, or a range of sensitivity levels, e.g. plus or minus 1 two-fold concentration for broth dilution tests.

A variety of techniques may also be used to determine the subtype of the isolate (Step 104). In one embodiment, multilocus sequence typing (MLST) is used to sequence the genome of the isolates at issue. It is to be understood that the discussion of MLST here is for explicatory purposes, and does not foreclose the usage of other NGS technologies, such as amplified fragment length polymorphism (AFLP), pulsed-field gel electrophoresis (PFGE), ribotyping, PCR-based fingerprinting, and multilocus enzyme electrophoresis (MLEE), either by themselves or in combination with one or more of each other.

MLST is a procedure for characterizing isolates of a bacterial species using the sequences of 6-10 house-keeping genes (the exact number of house-keeping genes depends on the particular microbe at issue). For each house-keeping gene, the different sequences present within a bacterial species are assigned as distinct alleles and, for each isolate, the alleles at each of the 6-10 house-keeping genes define the allelic profile or sequence type (ST) of the isolate. For example, a species with 7 house-keeping genes can be unambiguously characterized by a series of seven integers which correspond to the alleles at the seven house-keeping loci.

In MLST the number of nucleotide differences between alleles is ignored and sequences are given different allele numbers whether they differ at a single nucleotide site or at many sites. The rationale is that a single genetic event resulting in a new allele can occur by a point mutation (altering only a single nucleotide site), or by a recombinational replacement (that will often change multiple sites). Weighting according to the number of nucleotide differences between alleles would erroneously consider the allele to be more different than by treating the nucleotide changes as the result of a single genetic event.

Continuing the process, the result of the NGS operation is a sequence file (e.g., a Fastq sequence file). The sequencing output is typically aligned against a reference sequence using a publicly-available tool such as BWA or Samtools or, in some embodiments, may be subject to de novo assembly using algorithms such as VELVET to produce longer contiguous sequences.

Once the sequence data has been aligned and/or assembled, the results can be compared against a public or private database of genomic information to identify the particular subtype of the isolate. One such database is the PubMLST dataset, an open-source public database for molecular typing and microbial genome diversity available at http://pubmlst.org/. PubMLST contains a host of bacteria with defined house-keeping genes and their subtypes.

The results of the alignment/assembly step are blasted against a set of house-keeping genes chosen based on the PubMLST criteria for that species. The matching algorithm identifies a matching gene only if it is a 100% match (i.e., in both identity and length), assigns an allele number to that gene, and computes the allele numbers for all of the house-keeping genes of that species. The combination of the allele numbers is used to assign a subtype to the sequenced isolate. Although the preceding discussion focuses on NGS technologies, one of ordinary skill would recognize that many other underlying techniques may be used to generate the sequencing data used.

The display of the sensitivity of the subtypes to various antimicrobials (Step 108) utilizes the sensitivity/resistance profile for each isolate (Step 100) as well as the subtype information for the various isolates (Step 104). In one embodiment, a matrix of antimicrobials and subtypes is created and displayed which gives, e.g., the percentage of isolates which were found to be sensitive/resistant to the particular antimicrobial. In one embodiment, the average sensitivity of each subtype is computed and used as a threshold value for each subtype and/or each antimicrobial.

Some embodiments will present a matrix of every subtype identified in the hospital, although an operator may configure the interface to present a subset of the identified subtypes or a subset of the tested antimicrobials. For example, the subset(s) can be explicitly selected by an operator, or implicitly selected by specifying a particular time window for analysis and display (e.g., an antibiogram of all isolates from the last six months).

It would be apparent to one of ordinary skill that the order of steps in the preceding discussion is not necessarily canonical. For example, one of ordinary skill would recognize that an isolate can be subtyped prior to, contemporaneously with, or after its testing for sensitivity to one or more antimicrobials. Moreover, as embodiments typically concern themselves with multiple subtypes, one isolate may be subtyped and tested for sensitivity prior to, contemporaneously with, or after the subtyping and testing of one or more other isolates. Still other embodiments continue to update the graphical display after its initial presentation to allow for the addition of isolates that are subsequently subtyped and/or tested.

Figure 2:
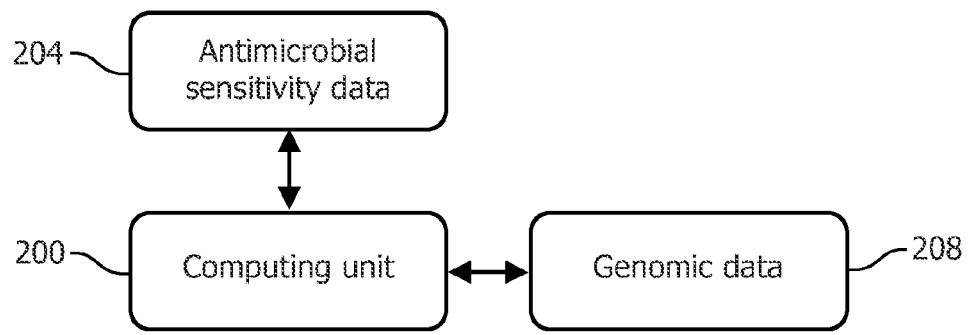
FIG. 2 illustrates a schematic representation of an embodiment of an apparatus for antibiogram generation.

FIG. 2 is a flowchart of an exemplary system for antibiogram generation. In this embodiment, a computing unit 200 is in communication with a source of antimicrobial sensitivity data for at least one isolate 204 and a source of genomic data 208.

The computing unit 200 may take a variety of forms in various embodiments. Exemplary computing units suitable for use with the embodiments described herein include desktop computers, laptop computers, virtual computers, server computers, smartphones, tablets, phablets, etc. Data sources 204, 208 may also take a variety of forms, including but not limited to structured databases (e.g., SQL databases), unstructured databases (e.g., Hadoop clusters, NoSQL databases), or other data sources running on a variety of computing units (e.g., desktop computers, laptop computers, virtual computers, server computers, smartphones, tablets, phablets, etc.). The computing units may be heterogeneous or homogeneous in various embodiments. In some embodiments, the data source 204 may be a piece of testing equipment that determines and stores the sensitivity of at least one isolate to at least one antimicrobial. In some embodiments, the data source 208 may be a publicly or privately accessible database of genomic data.

The components of the systems may be interconnected using a variety of network technologies being heterogeneous or homogenous in various embodiments. Suitable network technologies include but are not limited to wired network connections (e.g., Ethernet, gigabit Ethernet, token ring, etc.) and wireless network connections (e.g., Bluetooth, 802.11x, 3G/4G wireless technologies, etc.).

In operation, the computing unit 200 queries the antimicrobial data source 204 for information concerning the sensitivity of at least one isolate to at least one antimicrobial. The antimicrobial data source 204 may have such information because it has performed such a test on the isolate, or it may have received such information directly or indirectly (i.e., through data entry or transmission) from a piece of equipment that performed such testing.

In operation, the computing unit 200 queries the genomic data source 208 for information concerning the subtype of at least one isolate, often (though not necessarily) an isolate that is also the subject of a query to the antimicrobial data source 204. The genomic data source 208 may have such information stored locally, or it may contact other computing units to obtain the relevant subtype information as necessary.

Having received the requested sensitivity data and subtype data for one or more isolates, the computing unit 200 proceeds to generate a graphical presentation of the sensitivity data in combination with the subtype data, as is discussed in greater detail below.

As discussed above, the computing unit 200 may access either data source 204, 208 first or access both data sources contemporaneously. In some embodiments, computing unit 200 is local to an operator, i.e., being located on a local area network accessed by the operator. In other embodiments, computing unit 200 is accessed by an operator over yet another network connection (not shown), such as a wide area network or the Internet, and the graphical presentation is delivered to the operator over such network connection. In these embodiments, the computing unit 200 includes security and web server functionality customary to such remotely-accessed devices.

Figure 3:
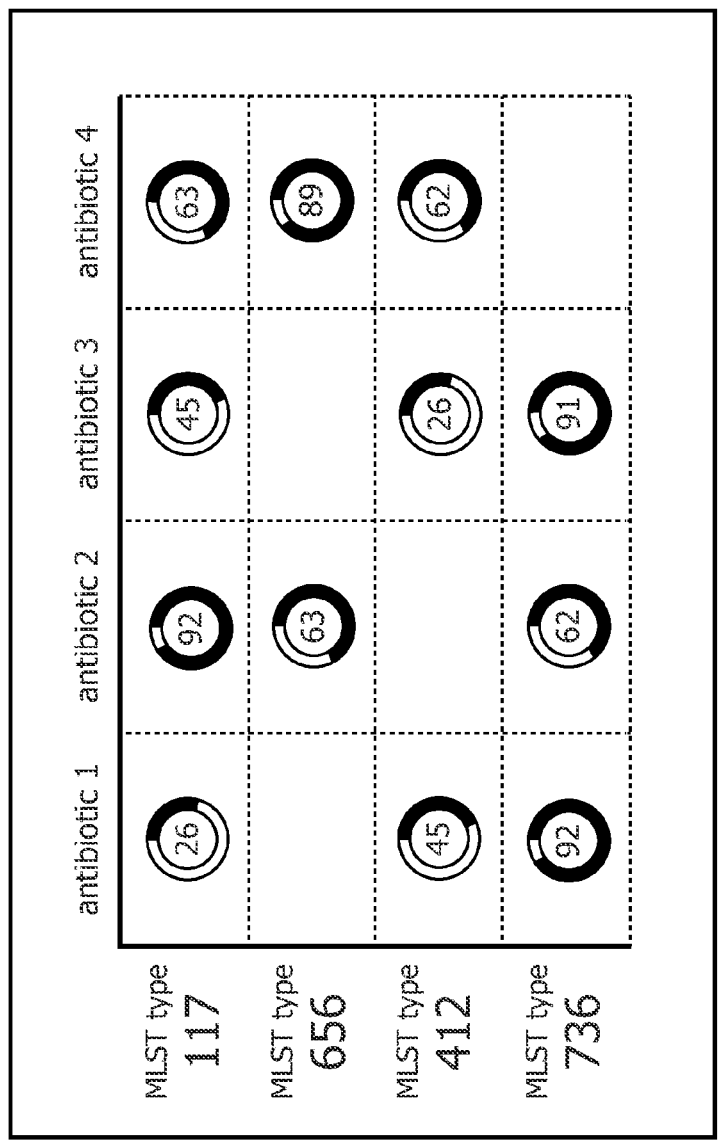
FIG. 3 is an example of a subtype-specific antibiogram generated by an embodiment.

FIG. 3 presents an exemplary subtype-specific antibiogram generated in accord with the principles described herein. This particular multi-subtype antibiogram is for *E. faecium*, a bacterium found in the human intestine that may be commensal (i.e., innocuous) but in this case is pathogenic.

Each row is a subtype of *E. faecium*, identified by MLST sequence type. Each column shows the sensitivity of that particular subtype to the identified anti-microbial. In this embodiment, each entry in the resultant matrix is a shaded circle and a number, although it is to be understood that other embodiments exist where the entry is a number, a shaded circle, a color, etc.

In this particular embodiment, the variations in each matrix entry compliments itself, i.e., in that the number, which represents the sensitivity/resistance ratio of the subtype to that particular antimicrobial, is also reflected in the level of shading of the circle as well as the color of the number and the color of the circle and its shading. Smaller numbers (i.e., indicative of a resistant subtype) also appear as a partially-shaded circle and one color range; larger numbers (i.e., indicative of a sensitive subtype) also appear as a more fully-shaded circle in a different color range. Moreover, in this particular range, sensitive and resistant subtypes are presented in full color, while subtypes with intermediate sensitivity to various antimicrobials (i.e., being neither particularly sensitive nor particularly resistant) are presented with less intensity.

It will be apparent to one of ordinary skill that any interface relying on any subset or combination of the preceding features, either by themselves or with other variations thereof (e.g., as a 3D matrix of columns, with each column reflective of a numerical value, in terms of its height, color, etc., as discussed above) may be incorporated into various embodiments. Although space prohibits an exhaustive list and/or discussion of all such possible variations, it is understood that they may be utilized among the various embodiments described herein.

For example, the sensitivity-to-resistance data for each subtype versus each anti-microbial could be displayed as a circle (solid or hollow) which could be color-coded based on the value of the sensitivity-to-resistance ratio. In another embodiment, these circles could be highlighted based on the percentage which was computed based on the available data. In other embodiments, the number of isolates from which the sensitivity-to-resistance ratio was computed can be displayed, which informs a specialist about the best drug for that particular strain based on previous knowledge.

Although the preceding discussion is limited to a multi-subtype/multi-antimicrobial antibiogram, it would be apparent to one of ordinary skill that the methods and systems discussed herein would also be useful for displays of virulence, neuropathy, joint pain, side effects, and other phenotypic correlations of patient behavior or patient clinical statistics (e.g., morbidity). It is also apparent to one of ordinary skill that, although the preceding discussion focuses on organism sub-types, various embodiments are suitable for use in analyzing any recognized subclassification of microbes that relies on genomic data, genotypic characteristics, or phenotypic characteristics, including but not limited to substrains.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed embodiments.

What is claimed is:

1. A computer-implemented method for generating a subtype-specific display, the method comprising:
    providing a computer processor configured to:
        (a) receive information concerning the sensitivity of at least one isolate to at least one antimicrobial;
        (b) receive information concerning the genomic subtype of the at least one isolate; and
        (c) provide a graphical display of at least one number representative of the sensitivity of the at least one isolate to an antimicrobial, the isolates organized by genomic subtype.

2. The computer-implemented method of claim 1 wherein receiving information concerning the genomic subtype of the at least one isolate comprises:
    (a) receiving data describing at least part of the genome of the at least one isolate;
    (b) comparing the received genomic data from the sequencing operation against a reference database; and
    (c) identifying a matching genomic subtype for the at least one isolate from the results of the comparison.

3. The computer-implemented method of claim 1 wherein receiving information concerning the sensitivity of the at least one isolate to at least one antimicrobial comprises receiving the results of an antimicrobial sensitivity test for the at least one isolate utilizing the at least one antimicrobial.

4. The computer-implemented method of claim 1 wherein providing a graphical display of the sensitivity of the at least one isolate to the at least one antimicrobial organized by genomic subtype comprises providing a graphical display in a matrix configuration with each row associated with one genomic subtype and each column associated with one antimicrobial.

5. The computer-implemented method of claim 1 wherein providing a graphical display of the sensitivity of the at least one isolate to the at least one antimicrobial organized by genomic subtype comprises providing a graphical display in a matrix configuration with each column associated with one genomic subtype and each row associated with one antimicrobial.

6. The computer-implemented method of claim 1 wherein providing a graphical display of the sensitivity of the at least one isolate to the at least one antimicrobial organized by genomic subtype comprises providing a graphical display of colored items in a matrix configuration.

7. The computer-implemented method of claim 1 wherein providing a graphical display of at least one number representative of the sensitivity of the at least one isolate to the antimicrobial comprises providing a graphical display of numbers in a column.

8. The computer-implemented method of claim 1 wherein each number is the prevalence of that isolate genomic subtype in a population in a particular timeframe and the sensitivity ratio for that isolate genomic subtype is displayed as a color or a shaded circle.

9. The computer-implemented method of claim 1 wherein each number is an average sensitivity for a plurality of isolates of a particular genomic subtype against a particular antimicrobial.

10. The computer-implemented method of claim 1 wherein each number is the sensitivity-to-resistance ratio for a genomic subtype against an antimicrobial.

11. A non-transitory machine-readable medium containing computer-executable instructions for performing a method for generating a subtype-specific display, the medium comprising:
(a) computer-executable instructions for receiving information concerning the sensitivity at least one isolate to at least one antimicrobial;
(b) computer-executable instructions for receiving information concerning the genomic subtype of the at least one isolate; and
(c) computer-executable instructions for providing a graphical display of at least one number representative of the sensitivity of the at least one isolate to an antimicrobial, the isolates organized by genomic subtype.

12. The non-transitory machine-readable medium of claim 11 wherein the computer-executable instructions for receiving information concerning the genomic subtype of the at least one isolate comprise:
(a) computer-executable instructions for receiving data describing at least part of the genome of the at least one isolate;
(b) computer-executable instructions for comparing the received genomic data from the sequencing operation against a reference database; and
(c) computer-executable instructions for identifying a matching genomic subtype for the at least one isolate from the results of the comparison.

13. The non-transitory machine-readable medium of claim 11 wherein the computer-executable instructions for receiving information concerning the sensitivity of the at least one isolate to at least one antimicrobial comprise computer-executable instructions for receiving the results of an antimicrobial sensitivity test for the at least one isolate utilizing the at least one antimicrobial.

14. The non-transitory machine-readable medium of claim 11 wherein the computer-executable instructions for providing a graphical display of at least one number representative of the sensitivity of the at least one isolate to the antimicrobial comprise computer-executable instructions for providing a graphical display in a matrix configuration with each row associated with one genomic subtype and each column associated with one antimicrobial.

15. The non-transitory machine-readable medium of claim 11 wherein the computer-executable instructions for providing a graphical display of at least one number representative of the sensitivity of the at least one isolate to the antimicrobial comprise computer-executable instructions for providing a graphical display in a matrix configuration with each column associated with one genomic subtype and each row associated with one antimicrobial.

* * * * *